United States Patent [19]

Motzkau

[11] Patent Number: Plant 6,412

[45] Date of Patent: Nov. 22, 1988

[54] AZALEA PLANT NAMED CACHET

[75] Inventor: Henry W. Motzkau, Lacey, Wash.

[73] Assignee: Yoder Brothers, Inc., Barberton, Ohio

[21] Appl. No.: 19,307

[22] Filed: Feb. 26, 1987

[51] Int. Cl.[4] ..... A01H 5/00

[52] U.S. Cl. ..... Plt./56

[58] Field of Search ..... Plt./55–57

*Primary Examiner*—James R. Feyrer

*Attorney, Agent, or Firm*—Schwartz, Jeffery, Schwaab, Mack, Blumenthal & Evans

[57] ABSTRACT

An Azalea plant named Cachet, particularly characterized by its fuchsia pink flower color, double flower form, evergreen foliage, early response, compact growth habit, ease of budding and by its excellent cooler and shipping tolerance.

1 Drawing Sheet

The present invention comprises a new and distinct cultivar of Azalea plant named Cachet obtained from crossing certain Azalea selections in a program of controlled hybridization by applicant in Lacey, Wash. The seed parent in the breeding program was identified by Code #2212, and the pollen parent by Code #2101.

The new cultivar is similar in many respects to the cultivar Solitaire, disclosed in U.S. Plant Pat. No. 3,171, having the same characteristics as Solitaire of:

1. Similar flower color.
2. Evergreen foliage.
3. Adapted to high temperatures.

The new cultivar is distinguished from Solitaire by the following characteristics:

1. More compact growth.
2. More ruffled flower form.
3. Faster to bud.
4. Quicker to flower and more uniform.

The new cultivar was selected by applicant in Lacey, Wash. from the seedling progeny of the above mentioned parents. Varietal worth was determined by flowering liners from cuttings taken from the initial selection in both a year round and natural season developmental flowering program over a period of 3 years. Stock growth was evaluated in the vicinity of Southern Florida.

The new cultivar was first asexually reproduced by applicant in Lacey, Wash. by cuttings, and subsequent propagation has taken place at Fort Myers, Fla. Cachet has been found to retain its distinctive characteristics through successive propagations.

When grown in the vicinity of Fort Myers, Fla., Cachet has a response described as early, and the following detailed description is based on observations made of the new cultivar from field grown plants in Fort Myers, Fla. The response time and blooming period may vary significantly with varying environmental conditions such as temperature and amount of daylight. Suggested flowering period is from December 15 through March in a natural season program and all 12 months in a year round controlled program.

The accompanying photograph shows in perspective view the unique features of the new cultivar, with colors being as true as possible with color illustrations of this type. Color references are to The Royal Horticultural Society Colour Chart. Where a particular color value is not precise, variations from the closest color value have been noted.

Botanical classification: *Rhododendron hybrida,* evergreen type.

Flower:

*Color.*—Reading location and season: In an office with a north window, florescent cool white tubes. Readings taken in November, at Fort Myers, Fla. between the hours of 10:00 a.m. and 2:00 p.m. General tonality: Fuchsia-pink 63B. Sepals first open: Dark pink 54A. Petals unfurl: Dark Pink 54A. Fully open: Inside: Fuchsia pink 63B. Reverse: Fuchsia pink 64D. Base of petals: Light pink 54D. Outer hose: Fuchsia pink 63B. Base of outer hose: Light pink 62D. Variations (dotted): Appear on 3 petals of each whorl (hose); dark reddish purple 58B.Text

*Bud.*—Size: Medium. Form: Conoidal. Opening habit: Looks somewhat like a rosebud.

*Bloom.*—Size: Medium, average 9 cm, range 8–10 cm. Borne: Several together, average 4, range 3–5. Form: Double.

*Blooming habit.*—Once, profusely. Response: Natural season: Early. Year round: All twelve months.

*Calyx.*—Hose.

*Peduncle.*—Length: 2 cm. Aspect: Hairy. Strength: Strong.

*Petals.*—Texture: Soft. Substance: Somewhat thin. Appearance: Inside: Satiny. Outside: Satiny. Form: Rounded with wavy margins giving a ruffled appearance. Arrangment: Imbricate. Fragrance: None. Persistance: Non shatter. Longevity (keeping quality): Greenhouse: 3 weeks. Home: 4 weeks.

Reproductive organs:

*Stamen-anthers.*—Rarely present, if present fused to petals. Immature: Reddish pink 58C. Mature: Brown 175A.

*Filaments.*—If present, columnar, reddish pink 58D.

*Style.*—Columnar, reddish pink 58C.

*Stigma.*—Normal, discoid. Immature: Light green 142A. Mature: Greyish orange 164B.

*Ovaries.*—Normal hairy.

Fruit: None.

Foliage:

*Type.*—Evergreen.

*Leaflets.*—Single.

*Size.*—Length: Average, 5 cm, range 4.5–5.5 cm. Width: Average, 2.25 cm, range 2.0–2.5 cm. Shape: Oblanceolate. Texture: Dull green. Rib and mid veins: Slightly depressed. Edge: Entire.

*Color (immature foliage).*—Upper surface: Darker than green 143A. Lower surface: Light green 138B.

*Color (mature foliage).*—Upper surface: Darker than dark green 136A. Lower surface: Light green 137C.

*Petiole.*—Medium length, light green.

Plant (bush):

*Growth habit.*—Compact.

*Breaking habit.*—Good.

*Rooting habit.*—Fair.

*Budding ease.*—Excellent.

*Uniformity of budding.*—Fair.

*Growth regulator.*—None.

*Stems (color).*—Immature wood: Light green 144B. Mature wood: Dark brown 165A.

*Responsiveness to day length and temperature.*—Buds easily and uniformly over a wide range of environmental conditions.

*Resistance to cylindrocladium.*—Good.

*Cooler tolerance.*—Excellent.

*Shipping tolerance.*—Excellent.

I claim:

1. A new and distinct cultivar of Azalea named Cachet, as described and illustrated, and characterized particularly as to novelty by its evergreen foliage, double flower form, fuchsia pink flower color, early response, compact growth habit, ease of budding, and excellent cooler and shipping tolerance.

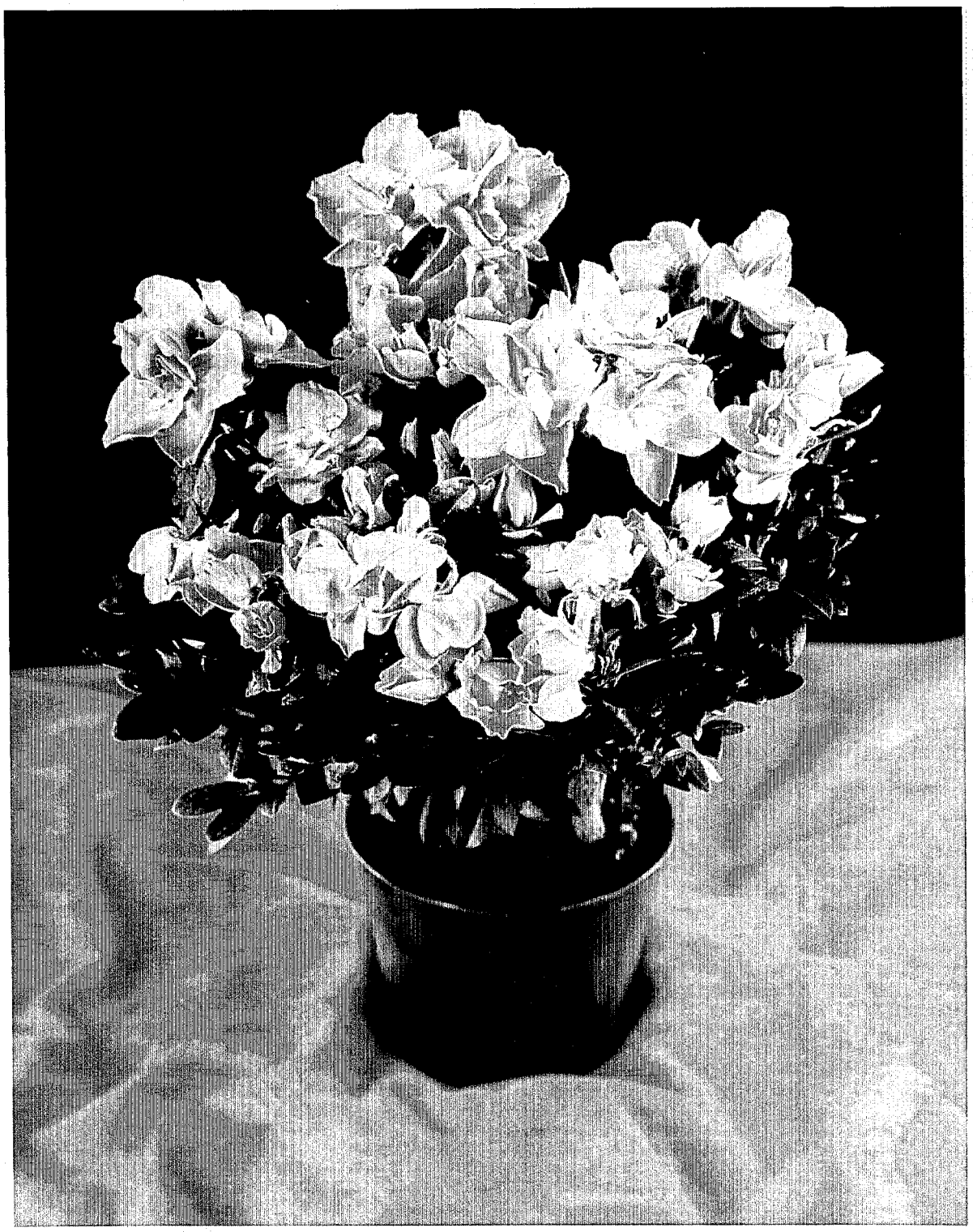

* * * * *